United States Patent [19]

Mattei

[11] 4,201,216

[45] May 6, 1980

[54] ABSORBABLE COATING COMPOSITION FOR SUTURES

[75] Inventor: Frank V. Mattei, Piscataway, N.J.

[73] Assignee: Ethicon, Inc., Somerville, N.J.

[21] Appl. No.: 10,761

[22] Filed: Feb. 9, 1979

Related U.S. Application Data

[63] Continuation-in-part of Ser. No. 751,002, Dec. 15, 1976, abandoned.

[51] Int. Cl.$^2$ .............................................. A61L 17/00
[52] U.S. Cl. .......................................... 128/335.5; 3/1
[58] Field of Search ............................ 128/335.5, 335; 428/262, 375, 378; 427/2

[56] References Cited

U.S. PATENT DOCUMENTS

| | | | |
|---|---|---|---|
| 4,027,676 | 6/1977 | Mattei | 128/335.5 |
| 4,043,344 | 8/1977 | Landi et al. | 128/335.5 |
| 4,047,533 | 9/1977 | Perciaccante et al. | 128/335.5 |

Primary Examiner—Robert W. Michell
Assistant Examiner—Thomas J. Wallen
Attorney, Agent, or Firm—Wayne R. Eberhardt

[57] ABSTRACT

The tie-down properties of multifilament surgical sutures are improved by coating the suture with an absorbable composition comprising a mixture of from about 1 to 4 parts of an absorbable, film-forming polymer, and 1 to 4 parts of a substantially water-insoluble salt of a $C_6$ or higher fatty acid. Braided sutures coated with from 2 to 10 percent by weight of the composition are characterized by a smooth knot tie-down under both wet and dry conditions.

23 Claims, No Drawings

ABSORBABLE COATING COMPOSITION FOR SUTURES

CROSS REFERENCE

This application is a continuation-in-part of Ser. No. 751,002, filed Dec. 15, 1976, now abandoned.

BACKGROUND OF THE INVENTION

1. Field of the Invention

This invention relates to an absorbable composition useful as a coating and lubricating finish for surgical sutures. More particularly, this invention relates to a means for improving the tie-down properties of synthetic absorbable multifilament sutures by coating the sutures with an absorbable lubricating composition.

2. Description of Prior Art

Suture materials are generally classified as either absorbable or nonabsorbable, with each type of suture material being preferred for certain applications. Absorbable suture materials are preferred for internal wound repair in which the sewn tissues will hold together after healing without suture reinforcement and in which a nonabsorbed suture may promote tissue irritation or other adverse bodily reaction over an extended period of time. Suture materials are considered to be absorbable if they disappear from the sewn tissue within about a year after surgery, but many absorbable suture materials disappear within shorter periods.

The earliest available absorbable suture materials were catgut and extruded collagenous materials. More recently, absorbable sutures derived from synthetic polymers have been developed which are strong, dimensionally uniform, and storagestable in the dry state. Typical of such polymers are lactide homopolymers and copolymers of lactide and glycolide such as those disclosed in U.S. Pat. No. 3,636,956, and glycolide homopolymers such as those disclosed in U.S. Pat. No. 3,565,869, both patents being incorporated herein by reference.

Monofilament synthetic absorbable suture materials are generally stiffer than their catgut or collagen counterparts, and synthetic absorbable sutures are therefore usually employed in a multifilament, braided construction in order to provide the suture with the desired degree of softness and flexibility. Such multifilament sutures exhibit a certain degree of undesirable roughness or "grabbiness" in what has been termed their "tie-down" performance, i.e., the ease or difficulty of sliding a knot down the suture into place.

Multifilament nonabsorbable sutures such as braided sutures of polyethylene terephthalate, for example, can be improved with respect to tie-down performance by coating the external surface of the suture with solid particles of polytetrafluoroethylene and a binder resin as disclosed in U.S. Pat. No. 3,527,650. This procedure, however, is undesirable as applied to absorbable sutures because polytetrafluoroethylene is nonabsorbable and sutures coated therewith would leave a polymer residue in the sewn tissue, after the suture had absorbed.

Multifilament, nonabsorbable sutures can also be improved with respect to tie-down performance by coating them with a linear polyester having a molecular weight between about 1,000 and about 15,000 and at least two carbon atoms between the ester linkages in the polymer chain as disclosed in U.S. Pat. No. 3,942,532. This patent discloses that the aforementioned polyesters may also be used to coat absorbable synthetic sutures but does not consider that such coated sutures would not be totally absorbable.

U.S. Pat. No. 3,297,033 discloses that the synthetic absorbable sutures described therein may be coated with conventional suture coating materials such as a silicone or beeswax in order to modify the handling or absorption rate of the sutures. These coating materials are not readily absorbable, however, and will accordingly leave an undesirable residue in the tissue after the suture itself is absorbed.

Many other compounds have been proposed as textile treating agents to improve the lubricity and handling of both natural and synthetic filaments. U.S. Pat. No. 3,896,841 describes the treatment of collagen sutures with a hydroscopic agent and lubricant to provide a suture which permanently retains at least 10 percent by weight moisture. Sutures so treated are reported to have increased suppleness and reduced drag when passing through tissue. Fatty compounds and derivatives of fatty compounds are suggested as useful lubricating agents for such collagen sutures.

U.S. Pat. No. 3,982,543 discloses that multifilament, absorbable sutures may be lubricated/coated with a copolymer of lactide and glycolide in order to reduce the capillarity of the suture, and sutures so treated are reported to have improved run down.

Some of the lubricating agents of the prior art are effective to improve the handling and knot tie-down characteristics of dry sutures. Because of the nature of surgical procedures, however, sutures are generally exposed to body fluids or passed one or more times through moist tissue before tying, and an effective suture coating composition ideally provides wet tie-down characteristics substantially equivalent to those of the dry suture. The known lubricating compositions of the prior art have not been effective in improving both the wet and dry tie-down properties of multifilament sutures.

It is accordingly an object of the present invention to provide an absorbable, lubricating coating for multifilament sutures of braided, twisted or covered construction. It is a further object of this invention to provide an absorbable coating to improve the tie-down properties of such multifilament sutures. It is a yet further object of this invention to provide a wholly absorbable coated synthetic multifilament suture having improved and substantially equal dry and wet knot tie-down properties.

SUMMARY OF THE INVENTION

In accordance with the instant invention, there is provided as a coating for sutures, particularly synthetic absorbable multifilament sutures, an absorbable composition comprising a film-forming polymer and a substantially water-insoluble salt of a $C_6$ or higher fatty acid. The coating is preferably applied to the suture from a solvent solution to provide a final coating add-on of from about 2 to 10 percent by weight of the suture.

The film-forming polymer is preferably a copolymer of lactide and glycolide, while the fatty acid salt is preferably a calcium salt of a $C_6$ to $C_{22}$ fatty acid. The ratio of polymer to fatty acid salt in the coating composition may be within the range of about 1:4 to 4:1 parts by weight. The coating is particularly useful for improving the dry and wet tie-down smoothness of braided sutures prepared from homopolymers and copolymers of lactide and glycolide, and other absorbable polymers.

DESCRIPTION OF PREFERRED EMBODIMENT

The coating compositions of the instant invention may be applied to any suture material where it is desired to improve fiber lubricity, suture tie-down characteristics, or the like. The coating is particularly useful with synthetic absorbable multifilament sutures such as polylactide, polyglycolide, copolymers of lactide and glycolide, poly(p-dioxanone), poly(alkylene oxalate), and mixtures of such polymers with each other and with other compatible absorbable compositions as those described, for example, in U.S. Pat. Nos. 3,636,952 and 2,683,136, which patents are herewith incorporated herein by reference. Preferred suture compositions derived from lactide and glycolide are sometimes referred to herein as simply homopolymers and copolymers of lactide and glycolide.

In a preferred embodiment of the present invention, the coating is applied to the suture surface as a solution and/or dispersion of the polymer and fatty acid salt in a volatile solvent such as acetone and solidification of the coating on the suture is accomplished by volatilizing the solvent. The coating may be applied to the suture by any suitable process such as passing the suture through a solution of the coating composition, or past a brush or applicator wetted with the solution, or past one or more spray nozzles dispensing the solution as droplets. The suture wetted with the coating solution is subsequently passed through or held in a drying oven for a time and at a temperature sufficient to volatilize the solvent.

In place of a coating solution, the coating composition may be applied as a melt of the constituents thereof, and in this case solidification takes place by cooling. The melt of the coating composition should, of course, be at a temperature below the melting temperature of the suture material, and this embodiment of the invention can be used only when the coating composition melts at relatively low temperatures.

The coating composition may also be applied to the suture as a solid by passing the suture over or between solid blocks of the coating composition which is then transferred to the surface of the suture by a rubbing action, possibly accompanied by localized melting.

In coating multifilament sutures with the compositions of this invention, it is not necessary that every filament within the suture be individually or completely coated. In most instances, however, the coating composition will penetrate into the suture structure, particularly when the coating composition is applied as a solvent solution.

Suitable film formers useful in the coating compositions of this invention include homopolymers and copolymers of lactide and glycolide, i.e., polylactide, polyglycolide, and copolymers of lactide and glycolide with each other and with other reactive monomers; poly (p-dioxanone), poly(alkylene oxalate), copolymers of vinyl acetates with unsaturated carboxylic acids such as crotonic, acrylic, and methacrylic acids; water soluble or dispersible cellulose derivatives such as methyl cellulose, hydroxymethyl cellulose and carboxymethyl cellulose; natural gums; ethylene oxide polymers; polyacrylamide; collagen; gelatin; polyamino acids; polyvinyl alcohol; polyvinyl pyrrolidone; absorbable conjugated unsaturated triglycerides such as dehydrated castor oil, and mixtures of such polymers. Particularly preferred film-forming polymers are the copolymers of lactide and glycolide which contain from about 15 to 85 percent lactide, and have an inherent viscosity of from about 0.5 to 4.0 measured as a 0.1 percent solution in hexafluoroisopropanol at 25° C. These polymers are water-insoluble, rapidly absorbable, and soluble in many common organic solvents such as acetone, chloroform, toluene, xylene, and 1,1,2-trichloroethane which facilitates their application to the suture as solutions.

The fatty acid salts useful in the coating compositions of the present invention includes the calcium, magnesium, barium, aluminum, and zinc salts of $C_6$ and higher fatty acids, particularly those having from about 12 to 22 carbon atoms and mixtures thereof. The calcium salts of stearic, palmitic and oleic acids are particularly preferred for use in the present invention.

The ratio of the film-forming polymer and the fatty acid salt in the coating composition may vary depending upon the specific components selected and the particular suture being coated. In general, the preferred ratio of polymer to salt is within the range of 2:1 to 1:2 by weight, although useful compositions are obtained over a wider range of from about 1:4 to 4:1 parts by weight.

With sutures composed of homopolymers or copolymers of lactide and glycolide, the film former in the coating composition is preferably polylactide or a copolymer of lactide and glycolide containing at least about 15 percent lactide, and preferably having different solubility characteristics than the suture. For example, a suture made of a lactide-glycolide copolymer containing about 10 percent of dilactyl moieties may be coated with a composition containing, as a film former, a lactide-glycolide copolymer containing about 65 percent of dilactyl moieties, which copolymer is more readily soluble in common organic solvents than the suture material.

The film former in the coating composition may, if desired, be the same composition as the suture provided that precautions are taken to avoid dissolving the suture when the coating composition is applied. This can be done by utilizing a coating composition in which the film former is a finely divided suspension in a nonsolvent liquid, or by utilizing a coating composition in which the film former is in solution at substantially saturation levels and the contact time of the suture with the coating composition is short before the solvent is driven off.

Where the compositions of the suture and the film former are identical, and in other instances where the suture material may be subject to some surface dissolution and/or surface swelling or softening by reason of the action of the film former solvent thereon, there may be a gradual transition between the substrate composition and the coating composition rather than a sharp interface between them. There may also be some weakening of the suture accompanying the application of such coating compositions.

The coating composition may, if desired, also contain components other than those discussed above for other useful purposes including dyes, antibiotics, antiseptics, anesthetics and anti-inflammatory agents.

The amount of coating composition applied to the fiber, or the coating add-on, will vary depending upon the construction of the fiber, e.g., the number of filaments and tightness of braid or twist, and the nature of the coating material, e.g., melt, solution or solid. In general, the coating composition applied to a braid will constitute from about 5 to about 10 percent by weight of the coated fiber, but coating composition addon may range from as little as about 2 percent by weight to as much as about 15 percent or higher in some cases. As a practical matter, and for reasons of economy and general performance, it is generally preferred to apply the minimum amount of coating composition consistent with good tie-down performance, and this level of add-on is readily determined experimentally for any particular fiber-coating system.

The improvement in tie-down properties imparted to synthetic absorbable sutures may be determined semi-quantitatively by comparing the feel of coated and uncoated sutures during the act of tying down a single throw knot. Such comparisons are preferably made on both wet and dry sutures since many suture materials have different tie-down properties when tested wet or dry. Suture tie-down roughness is graded from 0 to 10 with 0 being comparable to an uncoated suture and 10 indicating no detectable roughness.

Suture tie-down properties are evaluated dry after the sutures have been conditioned for at least 2 days in a vacuum drying oven at room temperature and 100 microns absolute pressure, and wet after being immersed in water at 25° C. for 1 minute. Roughness values above 4 are considered acceptable, while values of 7 or higher are comparable to conventional silicone coated silk and are considered fully satisfactory.

The following examples are provided to further illustrate and demonstrate the method and product of the present invention. Unless otherwise stated, all parts and percentages are by weight.

EXAMPLE 1

Forty-five parts of a low molecular weight ($\eta$inh 1.5 in HFIP) lactide/glycolide copolymer [65 mol % L(−) lactide and 35 mol % glycolide] and forty-five parts of calcium stearate* were placed in a porcelain pebble mill with 810 parts of 1,1,2-trichloroethane. Dissolving of the lactide/glycolide copolymer and dispersion of the calcium stearate were accomplished simultaneously by milling the mixture for two days. The solution/dispersion (Brookfield viscosity of 218 CPS at 35° C.) was then transferred to a suture coating bath. A size 3-0 braided suture of 90/10 (weight percent) glycolide/lactide copolymer was coated with the composition by passing the suture through the mixture while using a folded felt pad to wipe excess material from the suture as it exited the coating bath. The suture was coated at a speed of 8 feet per minute which provided an immersion time of about 5 seconds in the coating bath. After passing through the coating bath and the felt wiping pads, the suture immediately entered a drying tower where enough solvent was removed to render the suture tack free by the time the first guide was contacted. Drying was completed by winding the coated braid on a spool and keeping it in vacuum at 100 microns for two days. The coating solids pick-up was determined to be 5.3% of the uncoated braid. The suture was finished by winding the coated braid on an annealing rack under mild tension and heating 10 minutes at 110° C.

*Calcium stearate, a commercial food grade product consisting of about ⅓ $C_{16}$ and ⅔ $C_{18}$ fatty acid, with small amounts of $C_{14}$ and $C_{22}$ fatty acids.

Using afore described semi-quantitative smoothness-of-tie-down test, the coated braid in a single throw knot tie-down rated 8–9 dry, and 8 wet. The tensile strength of the coated braid was 9.9 lbs. under straight tension and 5.4 lbs. knotted, while in the uncoated control, tensiles were 9.9 lbs. and 5.8 lbs., respectively. Braided synthetic absorbable sutures coated in a similar manner were sterilized with ethylene oxide and implanted in animals. After 21 days, the strength of the coated braid was the same as in the uncoated control, and absorption was almost complete at 90 days, indicating that the coating composition or method of application had no significant effect on suture tensile strength or absorbability.

EXAMPLE 2

Using a coating solution/dispersion identical in composition to that in Example 1 except that total solids were 6% rather than 10%, the glycolide/lactide braided suture was coated by the same method. After vacuum drying, the coating solids pick-up was found to be 2.9% based on the uncoated braid.

As in Example 1, the suture was finished by heating the dry coated braid on an annealing rack at 110° C. for 10 minutes. After ethylene oxide sterilization, smoothness-of-tie-down was 7 dry and 6 wet. Tensile strengths were 10 lbs. and 5.4 lbs. straight and knot, respectively. Implantation in animals showed the same strength retained at 21 days as for the uncoated control. At 90 days post implantation, absorption was complete and tissue reaction was minimal throughout the test period.

EXAMPLE 3

The procedure of Example 2 was repeated by coating a size 4-0 braided suture comprised of poly(p-dioxanone) polymer with the 6% solids coating solution/dispersion composition. The coating solids pick-up was about 4% based on the weight of the uncoated suture. After drying, suture tie-down was tested and rated as excellent, being comparable to standard waxed silk suture material.

EXAMPLE 4

Twenty-five parts of a low molecular weight ($\eta$inh 1.5 in HFIP) lactide/glycolide copolymer [65 mol % L(−) lactide and 35 mol % glycolide] and twenty-five parts of magnesium stearate were placed in a flask with 360 parts of 1,1,2-trichloroethane and 90 parts by weight of chloroform. Solution of the polymer and dispersion of the stearate were obtained by stirring the mixture for about one week, resulting in a mixture having Brookfield viscosity of 299 CPS.

Using the methods described in Example 1, the glycolide/lactide braided suture was coated, and dried, and coating pick-up was determined to be 8.1% based on the uncoated suture. Using the smoothness-of-tie-down test described in Example 1, the dry and wet both rated 4–5.

EXAMPLE 5

Twenty-five parts of a low molecular weight ($\eta$inh 1.5 in HFIP) lactide/glycolide copolymer [65 mol % L(−) lactide and 35 mol % glycolide] and twenty-five parts of zinc stearate were placed in a flask with 360 parts of 1,1,2-trichloroethane and 90 parts by weight of chloroform. Solution and dispersion were obtained as in Example 3 to yield a coating composition having a viscosity of 139 CPS.

Using the methods described in Example 1, the glycolide/lactide braided suture was coated with 6.1% of coating solids based on the uncoated suture. Using the smoothness-of-tie-down test, the dry suture rated 5 while the wet suture rated 4.

EXAMPLE 6

Seven and one-half parts of the same lactide/glycolide copolymer described in the above examples and seven and one-half parts of calcium palmitate were placed in a flask containing 108 parts of 1,1,2-trichloroethane and 27 parts of chloroform. The polymer and palmitate salt were dissolved and dispersed by stirring vigorously several days.

Using methods of application and finishing described in Example 1, the glcyolide/lactide braided suture was coated with the solution/dispersion, and after drying, was found to have picked up 5.4% coating solids.

Using the smoothness-of-tie-down test, the dry and wet sutures rated 8 and 7, respectively.

EXAMPLE 7

Seven and one-half parts of the same lactide/glycolide copolymer described in the above examples and seven and one-half parts of calcium oleate were placed in a flask containing 108 parts of 1,1,2-trichloroethane and 27 parts of chloroform. The polymer and oleate salt were dissolved and dispersed by stirring vigorously several days.

Using methods of application and finishing described in Example 1, the glycolide/lactide braided suture was coated with the solution/dispersion, and after drying, was found to have picked up 9.8% coating solids.

Using the smoothness-of-tie-down test, the dry and wet sutures rated $5\frac{1}{2}$ and $4\frac{1}{2}$, respectively.

EXAMPLE 8

Calcium salts of $C_6$ (caproic), $C_8$ (caprylic), $C_{10}$ (capric), $C_{11}$ (undecylenic) and $C_{12}$ (lauric) fatty acids were prepared and applied to the glycolide/lactide braided suture of Claim 1. After drying, suture tie-down properties were found to be significantly improved over the uncoated suture material. Metal salts of $C_6$ and higher saturated and unsaturated fatty acids are thus shown to be efficacious in the practice of the present invention.

EXAMPLE 9

A series of tests were run to evaluate various compounds suggested by the prior art as being useful as textile lubricants. Where specific compounds were identified as lubricants, these compounds were evaluated. Where the lubricants were identified only class, i.e., fatty esters, fatty ethers, or fatty alcohols, representative compounds of those classes which were considered most likely to be effective were selected. A coating composition consisting of a 1/1 mixture by weight of the selected lubricant and the lactide/glycolide copolymer of Example I was applied from a solvent to a single lot of size 2-0 braided suture of 90/10 glycolide/lactide copolymer using the procedure described in Example I.

Twelve lubricant materials were evaluated as identified in the Table below. Solutions or dispersions of the coating compositions were prepared to approximately 5 to 7.5 percent total solids in trichloroethane except where otherwise noted in the Table. Insoluble lubricants were dispersed by ball milling for at least 24 hours. Suture tie-down rating reported in the Table below was determined on ten samples of each coated suture with single throw overhand knots—5 samples dry and 5 samples wet. An uncoated suture (Sample 1) and a suture coated only with the lactide/glycolide copolymer (Sample 2) were evaluated as controls.

| Sample | Coating lubricant | Coating pick-up, % | Tie-down rating Dry | Wet |
|---|---|---|---|---|
| 1 | None - (Uncoated Control) | — | 0 | 0 |
| 2 | None - (Lactide/Glycolide Coated Control) | 3.5 | $\frac{1}{2}$ | $\frac{1}{2}$ |
| 3 | Stearic Acid | 3.3 | 1 | $\frac{1}{2}$ |
| 4 | Palmitic Acid | 3.2 | 1 | 1 |
| 5 | Oleic Acid | 3.2 | $\frac{1}{2}$ | $\frac{1}{2}$ |
| 6 | Tristearin | 3.1 | 1 | 1 |
| 7 | Castorwax[a] | 3.0 | 2 | 2 |
| 8 | Polyethylene Glycol Distearate | 3.1 | $7\frac{1}{2}$ | 1 |
| 9 | Myristyl Alcohol | 3.2 | $1\frac{1}{2}$ | 1 |
| 10 | Stearyl Alcohol | 2.9 | 1 | 1 |
| 11 | Glycerine[b] | 3.2 | $1\frac{1}{2}$ | $1\frac{1}{2}$ |
| 12 | Polyethylene Glycol (M.W. 20,000) | 3.5 | $6\frac{1}{2}$ | $1\frac{1}{2}$ |
| 13 | Talc | 3.2 | $1\frac{1}{2}$ | $1\frac{1}{2}$ |
| 14 | Beeswax | 3.1 | $\frac{1}{2}$ | $\frac{1}{2}$ |
| 15 | Calcium Stearate | 3.1 | $7\frac{1}{2}$ | 8 |

[a]Triglyceride of 12-hydroxystearic acid.
[b]Solvent was 72/28 w/w/ trichloroethane/methanol.

As apparent from the above results, coating with only the lactide/glycolide copolymer (Sample 2) produced practically no improvement in either dry or wet tie-down. Of the twelve lubricants evaluated, only polyethylene glycol distearate (Sample 8) and polyethylene glycol (Sample 12) produced any substantial improvement in dry tie-down, but the wet tie-down properties of these sutures were unsatisfactory. Only the suture coated with calcium stearate in accordance with the present invention (Sample 15) demonstrated substantial improvement in both dry and wet tie-down characteristics where approximately equal results were obtained.

While the foregoing specification and examples have been directed to coating absorbable multifilament braided sutures, it will be readily appreciated that the coating may likewise be used with good results on absorbable monofilament sutures as well as on nonabsorbable monofilament and multifilament sutures.

Nonabsorbable sutures such as cotton, linen, silk, nylon, polyethylene terephthalate and polyolefins are normally coated with nonabsorbable compositions. Polyolefins are usually of monofilament construction while cotton, linen, silk and polyester are usually of braided, twisted or covered multifilament construction. While there is usually no requirement that the coating on such sutures be absorbable, the composition of the instant invention may, nevertheless, be used as a lubricating finish for nonabsorbable sutures if desired.

In the above examples, the coating solution was applied to the final suture structure in order to provide a substantially continuous coating on at least the outward facing surfaces of the outer-most filaments of the braid. It is understood, however, that the coating solution may be applied, if desired, to the individual filaments before they are formed into strands or to the individual strands before they are formed into the final suture structure. Also, while all the above examples were conducted with size 3-0 braided suture prepared from a 90/10 weight percent glycolide/lactide copolymer, this was for the sake of convenience only, and invention is not limited as to suture size or composition, but may be practiced, for example, with sutures from size 9-0 to size 2 and larger, and with other suture materials. The foregoing examples are intended to be merely illustrative, and many modifications and variations thereof will be apparent to those skilled in the art.

I claim:

1. A synthetic, absorbable, multifilament suture having improved and substantially equal dry and wet tie-down properties, said suture being coated with from about 2 to 15 percent by weight of a composition comprising a mixture of a substantially water-insoluble, absorbable salt of a $C_6$ or higher fatty acid and an absorbable, film-forming polymer, the ratio of said fatty acid salt to said polymer being from about 1:4 to 4:1.

2. A suture of claim 1, wherein the fatty acid salt is the salt of calcium, magnesium, barium, aluminum, or zinc.

3. A suture of claim 1, wherein said higher fatty acid is selected from the group consisting of $C_{12}$ to $C_{22}$ fatty acids and mixtures thereof.

4. A suture of claim 3, wherein the fatty acid salt is the salt of calcium or magnesium.

5. A suture of claim 4, wherein the fatty acid comprises a mixture of stearic and palmitic acid.

6. A suture of claim 1, wherein said film-forming polymer is selected from the group consisting of homopolymers and copolymers of poly(p-dioxanone), poly(alkylene oxalate), lactide, and glycolide, copolymers of vinyl acetate with unsaturated carboxylic acids, water soluble or dispersible cellulose derivatives, natural gums, ethylene oxide polymers, polyacrylamide, polyvinyl alcohol, polyvinyl pyrrolidone, gelatin, collagen, polyamino acids, conjugated unsaturated triglycerides, and mixtures thereof.

7. A suture of claim 1, wherein said film-forming polymer is a copolymer of lactide and glycolide containing from about 15 to 85 mole percent dilactyl units.

8. A suture of claim 7, wherein said lactide/glycolide copolymer has an inherent viscosity of from about 0.5 to 4.0 measured as a 0.1 percent solution in hexafluoroisopropanol at 25° C.

9. A suture of claim 8, wherein the lactide/glycolide copolymer contains about 65 mole percent dilactyl units.

10. A suture of claim 9, wherein the fatty acid salt comprises a mixture of calcium palmitate and calcium stearate.

11. A suture of claim 10, wherein the ratio of the fatty acid salt to lactide/glycolide polymer is between about 1:2 and 2:1.

12. A suture of claim 11, coated with from about 5 to 10 percent of the said mixture.

13. A suture of claim 1, wherein the synthetic absorbable suture is comprised of homopolymers or copolymers of lactide and glycolide.

14. A suture of claim 13, wherein said suture is comprised of a copolymer of 10 weight percent lactide and 90 weight percent glycolide.

15. A suture of claim 14, wherein the multifilament suture is a braided suture.

16. A suture of claim 1, wherein the synthetic absorbable suture is composed of poly(p-dioxanone).

17. A suture of claim 16, wherein the multifilament suture is a braided suture.

18. The method of claim 17, wherein said suture is composed of poly(p-dioxanone).

19. A method for imparting improved and substantially equal dry and wet tie-down properties to a multifilament suture which comprises coating said suture with from about 2 to 15 percent by weight on a dry basis of a composition comprising a mixture of a substantially water-insoluble, absorbable salt of a $C_6$ or higher fatty acid and an absorbable, film-forming polymer in a volatile solvent, the ratio of said fatty acid salt to said polymer being from about 1:4 to 4:1, and thereafter drying said coated suture to remove substantially all the solvent.

20. The method of claim 19, wherein the fatty acid salt is the salt of calcium, magnesium, barium, aluminum, or zinc.

21. The method of claim 19, wherein said higher fatty acid is selected from the group consisting of $C_{12}$ to $C_{22}$ fatty acids and mixtures thereof.

22. The method of claim 19, wherein said film-forming polymer is selected from the group consisting of homopolymers and copolymers of poly(p-dioxanone), poly(alkylene oxalate), lactide and glycolide, copolymers of vinyl acetate with unsaturated carboxylic acids, water soluble or dispersible cellulose derivatives, natural gums, ethylene oxide polymers, polyacrylamide, polyvinyl alcohol, polyvinyl pyrrolidone, gelatin, collagen, polyamino acids, conjugated triglycerides, and mixtures thereof.

23. The method of claim 19, wherein said suture is composed of an absorbable synthetic polymer selected from the group consisting of homopolymers and copolymers of lactide and glycolide.

* * * * *